United States Patent
Patel et al.

(10) Patent No.: US 10,485,742 B2
(45) Date of Patent: Nov. 26, 2019

(54) RHEOLOGICAL STABILIZATION THROUGH MIXED HUMECTANT SYSTEMS IN A ZINC TOOTHPASTE

(71) Applicant: Colgate-Palmolive Company, New York, NY (US)

(72) Inventors: Neeta Atul Patel, Monmouth Junction, NJ (US); Gregory Szewczyk, Flemington, NJ (US); Andre Morgan, Robbinsville, NJ (US); Melissa Muir, Lopatcong, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/828,787

(22) Filed: Dec. 1, 2017

(65) Prior Publication Data

US 2019/0167547 A1    Jun. 6, 2019

(51) Int. Cl.

| | |
|---|---|
| *A61K 8/27* | (2006.01) |
| *A61K 8/44* | (2006.01) |
| *A61K 8/34* | (2006.01) |
| *A61Q 11/00* | (2006.01) |
| *A61K 8/81* | (2006.01) |
| *A61K 8/24* | (2006.01) |
| *A61K 8/86* | (2006.01) |
| *A61K 8/36* | (2006.01) |
| *A61K 8/20* | (2006.01) |

(52) U.S. Cl.
CPC ............... *A61K 8/27* (2013.01); *A61K 8/345* (2013.01); *A61K 8/44* (2013.01); *A61K 8/8111* (2013.01); *A61K 8/86* (2013.01); *A61Q 11/00* (2013.01); *A61K 8/20* (2013.01); *A61K 8/24* (2013.01); *A61K 8/36* (2013.01); *A61K 2800/20* (2013.01); *A61K 2800/58* (2013.01)

(58) Field of Classification Search
CPC ... A61K 8/27; A61K 8/21; A61K 8/24; A61K 8/44; A61K 8/8176; A61K 8/8182; A61K 2800/58; A61Q 11/00; A61Q 11/02
See application file for complete search history.

(56) References Cited

U.S. PATENT DOCUMENTS

| | | | |
|---|---|---|---|
| 5,188,821 A | 2/1993 | Gaffar et al. | |
| 5,192,531 A | 3/1993 | Gaffar et al. | |
| 5,370,865 A * | 12/1994 | Yamagishi ............ | A61K 8/347 424/49 |
| 9,913,784 B2 | 3/2018 | Szewczyk et al. | |
| 2015/0328118 A1 | 11/2015 | Pan et al. | |
| 2017/0172870 A1 | 6/2017 | Szewczyk et al. | |

FOREIGN PATENT DOCUMENTS

| | | | |
|---|---|---|---|
| WO | WO 2014/098824 | * | 2/2014 |
| WO | WO 2015195124 | * | 12/2015 |

OTHER PUBLICATIONS

International Search Report and Written Opinion of the International Searching Authority in International Application No. PCT/US2017/064147, dated Mar. 14, 2018.

* cited by examiner

*Primary Examiner* — Lezah Roberts

(57) ABSTRACT

Disclosed herein are oral care compositions comprising a zinc amino acid halide complex, and a humectant system comprising polyethylene glycol and propylene glycol as structuring humectants, which compositions have improved rheological stability. Methods of making and using the compositions are also provided.

20 Claims, No Drawings

RHEOLOGICAL STABILIZATION THROUGH MIXED HUMECTANT SYSTEMS IN A ZINC TOOTHPASTE

FIELD OF THE DISCLOSURE

This disclosure relates to oral care compositions comprising a zinc amino acid halide complex (ZLC), and a humectant system which provides improved rheological stability. Methods of making and using the compositions are also provided.

BACKGROUND

Polyethylene glycol (PEG) and propylene glycol (PG) are very commonly used humectants/dispersants in toothpaste compositions because of their solubility in water and flexibility as great binders without having significant impact on aesthetic attributes such as foam. Often a mixed humectant system consisting of PEG and PG will be employed to maintain a toothpaste formula free from crystallization. These humectants have previously never been demonstrated to have any interaction or impact the toothpaste compositions rheologically. Nevertheless, the present disclosure has demonstrated their significant impact on rheology of the toothpaste compositions. Experiments indicate that PEG and PG do not remain innocuous in the formulation but rather interact strongly with the zinc species and water present to impact rheology of the toothpaste compositions such as viscosity. The interaction of PEG and PG with zinc and water surprisingly results in improved rheology, texture of the compositions, and thereby, stability of the compositions.

BRIEF SUMMARY

While oral care compositions comprising the ZLC complex are known, it has been challenging to formulate compositions comprising this complex which have good long-term stability and yield stress. However, the present invention has surprisingly improved stability of and yield stress of toothpaste compositions comprising the ZLC complex by incorporation of a humectant system that include PEG and PG as structuring humectant.

The present disclosure thus provides in one embodiment of oral care compositions, for example a toothpaste composition, which comprises a zinc-amino acid complex, e.g., a zinc-amino acid-halide complex such as zinc-lysine-chloride complex, e.g., ZLC, and further comprising a humectant system comprising a structuring humectant, wherein the structuring humectant is PEG in an amount of 1-10% by weight of the toothpaste composition and PG in an amount of 1-10% by weight of the toothpaste composition.

The present disclosure further provides methods of using the compositions disclosed herein to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying a composition of the invention to the teeth.

The present disclosure further provides methods of making the compositions disclosed herein comprising combining a zinc ion source (e.g., ZnO), an amino acid (e.g., a basic amino acid, e.g., arginine or lysine, in free or salt form), and optionally a halide source, for example combining zinc oxide and lysine hydrochloride in aqueous solution, e.g. at a molar ratio of Zn:amino acid of 1:1 to 1:3, e.g., 1:2 and Zn:halide where present of 1:1 to 1:3, e.g., 1:2; optionally isolating the ionic complex thus formed as a solid; and admixing with an oral care base, e.g., a toothpaste, which further comprises PEG and PG.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The zinc-amino acid complexes described herein are disclosed in U.S. Patent Application Publication 2015/0328118 and PCT Publication WO 2014/098826, the contents of each of which are hereby incorporated by reference in their entireties.

The present disclosure provides, in a first embodiment, a toothpaste composition (Composition 1), comprising zinc in complex with an amino acid, e.g., a zinc-amino acid-halide complex, PEG, and PG in an amount of 1-10% by weight of the composition. In further embodiments, the disclosure provides:

1.1. Composition 1 wherein the amino acid is selected from lysine, glycine, and arginine, in free or orally acceptable acid addition salt form, e.g., hydrochloride form.
1.2. Composition 1 or 1.1 wherein the amino acid is a basic amino acid, e.g., arginine or lysine, in free or orally acceptable salt form.
1.3. Any of the foregoing compositions, wherein the amino acid is lysine in free or salt form.
1.4. Any of the foregoing compositions, wherein the amino acid is lysine monohydrochloride in an amount of about 4.72% by weight of the composition.
1.5. Any of the foregoing compositions further comprising a halide in ionic association with the zinc and amino acid and/or comprising a halide atom in coordination with the zinc and amino acid.
1.6. Any of the foregoing compositions wherein the molar ratio of Zn: amino acid is from 3:1 to 1:5, e.g., about 1:2 and the molar ratio of Zn: halide where present is from 3:1 to 1:3, e.g., about 1:2.
1.7. Any of the foregoing compositions wherein the zinc—amino acid complex is formed, in whole or in part, in situ after the composition is applied.
1.8. Any of the foregoing compositions wherein the zinc—amino acid complex is formed, in whole or in part, in situ after the composition is formulated.
1.9. Any of the foregoing compositions, wherein zinc is present in an amount of 0.05 to 10% by weight of the composition, optionally at least 0.1, at least 0.2, at least 0.3, at least 0.4, at least 0.5, at least 1, at least 2, at least 3, or at least 4 up to 10% by weight of the composition, e.g., 0.5-1, or 2, 2.5, 3 or 4 or 5, e.g. 1-3%, e.g., 2-2.7% by weight of the composition, e.g., about 0.84% by weight of the composition.
1.10. Any of the foregoing compositions, wherein amino acid is present in an amount of 0.05 to 30% by weight of the composition, optionally at least 0.1, at least 0.2, at least 0.3, at least 0.4, at least 0.5, at least 0.8, at least 1, at least 2, at least 3, at least 4, at least 5, at least 10, at least 15, at least 20 up to 30% by weight, e.g., 0.1-10%, 0.5, or 1, or 2, or 3, or 4-5%, about 4.72%, 0.5-2%.

1.11. Any of the foregoing compositions, wherein a molar ratio of zinc to amino acid is 2:1 to 1:4, optionally 1:1 to 1:4, 1:2 to 1:4, 1:3 to 1:4, 2:1 to 1:3, 2:1 to 1:2, or 2:1 to 1:1, e.g., about 1:2 or 1:3.

1.12. Any of the foregoing compositions comprising a halide in ionic association with the zinc and amino acid, and/or comprising a halide atom in coordination with the zinc and amino acid wherein the halide is selected from the group consisting of fluorine, chlorine, and mixtures thereof.

1.13. Any of the foregoing compositions wherein the zinc amino acid complex is a zinc lysine chloride complex (e.g., $(ZnLys_2Cl)^+Cl^-$ or $(ZnLys_3)^{2+}Cl_2$) or a zinc arginine chloride complex (e.g., $(ZnArg_2Cl)^+Cl^-$ or $(ZnArg_3)^{2+}Cl_2$).

1.14. Any of the foregoing compositions, wherein the zinc amino acid complex is a zinc lysine chloride complex, e.g., ZLC, e.g., a zinc lysine chloride complex having the chemical structure $[Zn(C_6H_{14}N_2O_2)_2Cl]^+Cl^-$, either in solution of the cationic cation (e.g., $[Zn(C_6H_{14}N_2O_2)_2Cl]^+$) and the chloride anion, or in solid salt form, e.g., crystal form, optionally in mono- or dihydrate form.

1.15. Any of the foregoing compositions, wherein the composition comprises from 1% to 10% by weight of zinc-amino complex, e.g. zinc-lysine complex, or ZLC complex, for example 2-8%, or 3-8%, or 4-8%, or 4-7%, or 4-6%, or 5-6%, or about 5.77%.

1.16. Any of foregoing toothpaste compositions, wherein PEG is present in an amount of 2%-4% by weight of the toothpaste composition and PG is present in an amount of 3%-5% by weight of the toothpaste composition.

1.17. Any of foregoing toothpaste compositions, wherein PEG is present in an amount of about 3 by weight of the toothpaste composition and PG is present in an amount of about 4% by weight of the toothpaste composition.

1.18. Any of foregoing toothpaste compositions, wherein PEG is PEG 600.

1.19. Any of foregoing toothpaste compositions, wherein humectant system comprising an additional humectant, e.g., selected from sorbitol, glycerin, xylitol, and mixtures thereof, e.g. comprising at least 20%, e.g., 20-80%, e.g., 30-60% of humectant.

1.20. Any of the toothpaste compositions, wherein the compositions comprise 0.1 to 5% by weight of linear-PVP, e.g., 0.5 to 5%, 0.5 to 4%, 0.5 to 3%, 0.5 to 2.5%, 0.5 to 2%, 1 to 2%, 1 to 1.5%, or about 1%, or about 1.5%.

1.21. Any of the foregoing toothpaste compositions, wherein the compositions comprise 0.1 to 5% by weight of cross-linked PVP, e.g., 0.5 to 5%, 0.5 to 4%, 0.5 to 3%, 0.5 to 2.5%, 0.5 to 2%, 1 to 2%, 1 to 1.5%, or about 1%, or about 1.5%.

1.22. Any of the foregoing toothpaste compositions comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 0.5-20%, e.g., 1-8%, e.g., 1-5%, e.g., 1-3%, e.g., about 2% by weight of the composition.

1.23. Any of the foregoing toothpaste compositions comprising an alkali metal tripolyphosphate salt, e.g., sodium or potassium tripolyphosphate, in an amount of 0.5-20% by weight, e.g., 1-5%, 2-5%, or 2-4%, or 2-3%, or 1-4%, or 1-3%, or 1-2% or about 2% by weight.

1.24. Any of the foregoing toothpaste compositions, wherein the compositions do not comprise an alkali metal pyrophosphate salt (e.g., tetrasodium or tetrapotassium pyrophosphate).

1.25. Any of the foregoing toothpaste compositions wherein sodium tripolyphosphate is the only polyphosphate salt present.

1.26. Any of the foregoing toothpaste compositions wherein sodium tripolyphosphate is the only polyphosphate salt present, in an amount of about 2% by weight of the composition.

1.27. Any of the foregoing toothpaste compositions, further comprising an organic or inorganic acid to reduce the pH, e.g., selected from one or more of phosphoric acid, hydrochloric acid, sulfuric acid, citric acid, tartaric acid, malic acid, maleic acid, fumaric acid, lactic acid, gluconic acid, benzoic acid, or the like, in an amount of from 0.05 to 5% by weight of the composition, or 0.1 to 2%, or 0.1 to 1%, or 0.1 to 0.75%, or 0.25 to 0.75%, or about 0.44%.

1.28. Any of the foregoing toothpaste compositions, further comprising hydrochloric acid, in an amount of from 0.05 to 5% by weight of the composition, or 0.1 to 2%, or 0.1 to 1%, or 0.1 to 0.75 or 0.5 or 0.4, or 0.3%, or 0.25 to 0.75%, or about 0.25%.

1.29. Any of the foregoing toothpaste compositions, further comprising phosphoric acid, in an amount of from 0.05 to 5% by weight of the composition, or 0.1 to 2%, or 0.1 to 1%, or 0.1 to 0.75%, or about 0.17%.

1.30. Any of the foregoing toothpaste compositions, wherein the composition comprises sodium tripolyphosphate and phosphoric acid.

1.31. Any of the foregoing toothpaste compositions, wherein the composition comprises linear-PVP, sodium tripolyphosphate and phosphoric acid.

1.32. Any of the foregoing toothpaste compositions, wherein the composition is a low-water composition, e.g., having a water content of less than 20% by weight, for example 5-20%, or 5-15%, e.g., 15%, or 5-11 or 12 or 13 or 14% by weight.

1.33. Any of the foregoing toothpaste compositions, wherein the zinc—amino acid complex is present in an effective amount, e.g., in an amount of 0.05-4% by weight of zinc relative to the composition, e.g., 0.1-3%, 0.2-2%, about 0.84%.

1.34. Any of the foregoing toothpaste compositions, wherein the composition comprises an abrasive, e.g., an effective amount of a silica abrasive, e.g., 5-30%, e.g., about, 5%, 7%, about 10%, and about 22%.

1.35. Any of the foregoing toothpaste compositions, wherein the composition comprises a silica abrasive/cleaning in an amount of 22%.

1.36. Any of the foregoing toothpaste compositions further comprising an effective amount of a fluoride ion source, e.g., providing 50 to 20,000 ppm fluoride, e.g., 1000 to 5000 ppm, e.g., about 3200 ppm.

1.37. Any of the foregoing toothpaste compositions further comprising an effective amount of a fluoride source, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.38. Any of the foregoing toothpaste compositions further comprising an effective amount of a fluoride source, wherein the fluoride source is sodium fluoride.

1.39. Any of the foregoing toothpaste compositions further comprising an effective amount of a fluoride source, wherein the fluoride source is sodium fluoride in an amount of 0.32%.

1.40. Any of the foregoing toothpaste compositions comprising buffering agents, e.g., sodium phosphate buffer (e.g., sodium phosphate monobasic and disodium phosphate).

1.41. Any of the foregoing compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from 0.3% to 4.5% by weight, e.g., 0.5 to 1, or 2 or 3 or 4%, e.g. 1-2% sodium lauryl sulfate (SLS), e.g., 1.75% SLS; and/or a zwitterionic surfactant, for example a betaine surfactant, for example cocamidopropylbetaine, e.g. in an amount of from about 0.1% to about 4.5% by weight, e.g. 0.5-2% cocamidopropylbetaine, e.g., about 1%.

1.42. Any of the foregoing compositions comprising SLS.

1.43. Any of the foregoing compositions comprising SLS in an amount of 1.75% by weight of the composition.

1.44. Any of the foregoing compositions comprising cocamidopropylbetaine.

1.45. Any of the foregoing compositions comprising cocamidopropylbetaine in an amount of 1.00% by weight of the composition 1.46. Any of the foregoing toothpaste compositions further comprising a viscosity modifying amount of one or more of polysaccharide gums, for example xanthan gum or carrageenan, carboxymethyl cellulose, silica thickener, and combinations thereof, e.g., xanthan gum.

1.47. Any of the foregoing toothpaste compositions further comprising xanthan gum in an amount of 0.1%.

1.48. Any of the foregoing toothpaste compositions comprising gum strips or fragments.

1.49. Any of the foregoing toothpaste compositions further comprising flavoring, fragrance and/or coloring.

1.50. Any of the foregoing toothpaste compositions comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), magnolol and its derivatives (e.g., isobutyl magnolol, isopropyl magnolol, tert-butyl magnolol, honokiol), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, octapinol and other piperidino derivatives, nicin preparations, chlorite salts; and mixtures of any of the foregoing; e.g., comprising triclosan or cetylpyridinium chloride.

1.51. Any of the foregoing toothpaste compositions further comprising a whitening agent, e.g., a selected from the group consisting of peroxides, metal chlorites, perborates, percarbonates, peroxyacids, hypochlorites, and combinations thereof.

1.52. Any of the foregoing toothpaste compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.53. Any of the foregoing toothpaste compositions further comprising a physiologically or orally acceptable potassium salt, e.g., potassium nitrate or potassium chloride, in an amount effective to reduce dentinal hypersensitivity.

1.54. Any of the foregoing toothpaste compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.

1.55. Any of the foregoing toothpaste compositions further comprising a breath freshener, fragrance or flavoring.

1.56. Any of the foregoing toothpaste compositions, wherein the pH of the composition is from pH 5 to pH 8.5, for example, from pH 5 to 7.5, or 5 to 7, or 5.5 to 7.5, or 5.5 to 7, or 6 to 8, or 6 to 7.5, or 6.5 to 8, or 6.5 to 7.5, or 6 to 7, or 6.5 to 7, or 6 to 6.5, or about 6, or about 6.5 or about 7 or about 7.6 or about 8.2.

1.57. A toothpaste composition comprising
  a. zinc in complex with an amino acid in an amount of about 5.77% by weight of the composition,
  b. a humectant system comprising a structuring humectant, wherein the structuring humectant is PEG in an amount of about 3% by weight of the composition and PG in an amount of about 4% by weight of the composition, and
  c. an effective amount of a fluoride ion source, e.g., about 0.32% by weight of the composition.

1.58. A toothpaste composition comprising
  a. zinc in complex with an amino acid in an amount of about 5.77% by weight of the composition,
  b. a humectant system comprising a structuring humectant, wherein the structuring humectant is PEG 600 in an amount of about 3% by weight of the composition and PG in an amount of about 4% by weight of the composition,
  c. an effective amount of a fluoride ion source, e.g., about 0.32% by weight of the composition, and
  d. silicas in an amount of about 22% by weight of the composition.
 1.59. A toothpaste composition comprising
  a. zinc in complex with an amino acid in an amount of about 5.77% by weight of the composition,
  b. a humectant system comprising a structuring humectant, wherein the structuring humectant is PEG 600 in an amount of about 3% by weight of the composition and PG in an amount of about 4% by weight of the composition,
  c. an effective amount of a fluoride ion source, e.g., about 0.32% by weight of the composition,
  d. silicas in an amount of about 22% by weight of the composition, and
  e. sodium tripolyphosphate in an amount of about 2% by weight of the composition.
 1.60. A toothpaste composition comprising
  a. zinc in complex with an amino acid,
  b. a humectant system comprising a structuring humectant, wherein the structuring humectant is PEG 600 in an amount of 1%-10% by weight of the composition and PG in an amount of 1%-10% by weight of the composition,
  c. an effective amount of a fluoride ion source,
  d. silicas,
  e. an additional humectant,
  f. a tripolyphosphate salt,
  g. an anionic surfactant,
  h. a zwitterionic surfactant, and
  i. a flavoring and sweetener.
 1.61. Any of the foregoing toothpaste compositions for use to reduce and inhibit acid erosion of the enamel, clean the teeth, reduce bacterially-generated biofilm and plaque, reduce gingivitis, inhibit tooth decay and formation of cavities, and/or reduce dentinal hypersensitivity.

The present disclosure further provides methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of a composition of the invention, e.g., any of Composition 1, et seq. to the teeth, and optionally then rinsing with water or aqueous solution sufficient to trigger precipitation of zinc oxide from the composition.

The present disclosure further provides methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of a composition of the invention, e.g., any of Composition 2, et seq. to the teeth, and optionally then rinsing with water or aqueous solution sufficient to trigger precipitation of zinc oxide from the composition.

The present disclosure further provides a method of making a toothpaste composition comprising a zinc amino acid complex, e.g., any of Composition 1, et seq. comprising combining a zinc ion source with an amino acid, in free or salt form (e.g., combining zinc oxide with lysine hydrochloride), in an aqueous medium, optionally isolating the complex thus formed in solid salt form, and combining the complex with the toothpaste base, which comprises a humectant system comprising a structuring humectant, wherein the structuring humectant is PEG in an amount of 1%-10% by weight of the toothpaste composition and PG in an amount of 1%-100% by weight of toothpaste composition, The present disclosure further provides a method of making a toothpaste composition comprising a zinc amino acid complex, e.g., any of Composition 2, et seq. comprising combining a zinc ion source with an amino acid, in free or salt form (e.g., combining zinc oxide with lysine hydrochloride), in an aqueous medium, optionally isolating the complex thus formed in solid salt form, and combining the complex with toothpaste base, which comprises sodium tripolyphosphate, and optionally further comprises an acid, e.g., phosphoric acid.

For example, in various embodiments, the present disclosure provides methods to (i) reduce hypersensitivity of the teeth. (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of Compositions 1, et seq., as described above to the oral cavity of a person in need thereof, e.g., one or more times per day. The invention further provides Compositions 1, et seq., for use in any of these methods.

Without intending to be bound by theory, it is believed that the formation of the zinc amino acid halide proceeds via formation of the zinc halide then coordination of amino acid residues around a central zinc. Using reaction of ZnO with lysine hydrochloride in water as an example, the zinc can react with lysine and/or lysine.HCl to form a clear solution of Zn-lysine-chloride complex ($ZnLys_3Cl_2$), wherein $Zn^{++}$ is located in an octahedral center coordinated with two oxygen and two nitrogen atoms in the equatorial plane coming from two lysine's carboxylic acids and amine groups respectively. The zinc is also coordinated to the third lysine via its nitrogen and carboxylic oxygen, at the apical position of the metal geometry.

In another embodiment, a zinc cation complexes with two amino acid residues and two chloride residues. For example, where the amino acid is lysine, the complex has the formula $[Zn(C_6H_{14}N_2O_2)_2Cl]^+Cl^-$. In this complex, Zn cation is coordinated by two lysine ligands with two N atoms from $NH_2$ groups and O atoms from carboxylic groups in an equatorial plane. It displays a distorted square-pyramidal geometry with the apical position occupied by a Cl atom. This novel structure gives rise to a positive cation moiety, to which a $Cl^-$ anion is combined to form an ionic salt.

Other complexes of zinc and amino acid are possible, and the precise form is dependent in part on the molar ratios of the precursor compounds, e.g., if there is limited halide, halide-free complexes may form, e.g. $ZnOLys_2$, having a pyramid geometry, with the equatorial plane that is same as the above compound (Zn is bound to two oxygen and two nitrogen atoms from different lysines), wherein the top of the pyramid is occupied by an O atom.

Mixtures of complexes and/or additional complex structures, e.g., involving multiple zinc ions based on the zinc structure, are possible and contemplated within the scope of the invention. When the complexes are in solid form, they may form crystals, e.g. in hydrated form.

Irrespective of the precise structure of the complex or complexes, however, the interaction of the zinc and the amino acid converts insoluble zinc oxide or zinc salts to a highly soluble complex at approximately neutral pH. With increasing dilution in water, however, the complex disassociates, and the zinc ion converts to insoluble zinc oxide. This precipitation occludes the dentinal tubules, thereby reducing hypersensitivity, and also provides zinc to the enamel, which reduces acid erosion, biofilm and plaque formation.

It will be understood that other amino acids can be used in place of lysine in the foregoing scheme. It will also be understood that, although the zinc, amino acid and optionally halide may be primarily in the form of precursor materials or in the form of an ionic complex, there may be some degree of equilibrium, so that the proportion of material which is actually in complex compared to the proportion in precursor form may vary depending on the precise conditions of formulation, concentration of materials, pH, presence or absence of water, presence or absence of other charged molecules, and so forth.

In some embodiments, the active zinc-amino acid complex is provided in a toothpaste. Upon brushing, the active is diluted by saliva and water, leading to precipitation and the formation of deposits and occluding particles.

The composition can include the zinc amino acid halide and/or precursors thereof. Precursors, which can react in situ with water to form the zinc amino acid halide, include (i) zinc and an amino acid hydrohalide, or (ii) zinc chloride and amino acid, or (iii) a zinc ion source, an amino acid, and a halogen acid, or (iv) combinations of (i), (ii), and/or (iii). In one embodiment, the zinc amino acid halide can be prepared at room temperature by mixing the precursors in a solution, such as water. The in situ formation provides ease of formulation. The precursors can be used instead of first having to form the zinc amino acid halide. In another embodiment, the water permitting formation of the zinc amino acid halide from the precursor comes from saliva and/or rinsing water that comes into contact with the composition after application.

The zinc amino acid halide complex is a water-soluble complex formed from the halide acid addition salt of zinc (e.g., zinc chloride) and an amino acid, or from the halide acid addition salt of an amino acid (e.g., lysine hydrochloride) and zinc ion source, and/or from combination of all three of a halogen acid, an amino acid, and a zinc ion source.

Examples of amino acids include, but are not limited to, the common natural amino acids, e.g.: lysine, arginine, glycine, serine, threonine, asparagine, glutamine, cysteine, selenocysteine, proline, alanine, valine, isoleucine, leucine, methionine, phenylalanine, tyrosine, tryptophan, aspartic acid, and glutamic acid. In some embodiments, the amino acid is a neutral or acidic amino acid, e.g., glycine.

The precipitation of zinc from the complex upon dilution with water is most notable when the complex is formed from a basic amino acid. Thus, where precipitation upon dilution is desired, a basic amino acid may be preferred. In some embodiments, therefore, the amino acid is a basic amino acid. By "basic amino acid" is meant the naturally occurring basic amino acids, such as arginine, and lysine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In certain embodiments, the amino acid is lysine or its salts. In other embodiments, the amino acid is arginine or its salts.

In various embodiments, the amino acid is present in an amount of 0.5 wt. % to 20 wt. % of the total composition weight, 0.5 wt. % to 10 wt. % of the total composition weight, for example, 1-5%, about 1.5 wt. %, about 4.72 wt. %, about 5 wt. % of the total composition weight in the case of a dentifrice.

The halide may be chlorine, bromine, or iodine, most typically chlorine. The acid addition salt of an amino acid and a halogen acid (e.g., HCl, HBr, or HI) is sometimes referred to herein as an amino acid hydrohalide. Thus, one example of an amino acid hydrohalide is lysine hydrochloride. Another is glycine hydrochloride.

The zinc ion source for combination with an amino acid halide or an amino acid optionally plus halogen acid in this case may be, e.g., zinc oxide or zinc chloride.

In certain embodiments, the amount of zinc amino acid halide complex in the composition is 0.05 to 10% by weight of the composition. In certain embodiments, precursors, e.g., zinc and amino acid hydrohalide, are present in amounts such that when combined into the zinc amino acid halide, the zinc amino acid halide would be present in an amount of 0.05 to 10% by weight of the composition. In either of these embodiments, the amount of the zinc amino acid halide can be varied for the desired purpose, such as a dentifrice or a mouthwash. In other embodiments, the amount of the zinc amino acid halide is at least 0.1, at least 0.2, at least 0.3, at least 0.4, at least 0.5, at least 1, at least 2, at least 3, or at least 4 up to 10% by weight of the composition. In other embodiments, the amount of the zinc amino acid halide is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, zinc is present in an amount of 0.05 to 10% by weight of the composition. In other embodiments, the amount of zinc is at least 0.1, at least 0.2, at least 0.3, at least 0.4, at least 0.5, at least 1, at least 2, at least 3, or at least 4 up to 10% by weight of the composition. In other embodiments, the amount of the zinc is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, amino acid hydrohalide is present in an amount of 0.05 to 30% by weight. In other embodiments, the amount is at least 0.1, at least 0.2, at least 0.3, at least 0.4, at least 0.5, at least 1, at least 2, at least 3, at least 4, at least 5, at least 10, at least 15, at least 20 up to 30% by weight. In other embodiments, the amount is less than 30, less than 25, less than 20, less than 15, less than 10, less than 5, less than 4, less than 3, less than 2, or less than 1 down to 0.05% by weight of the composition.

Where precursor materials are present, they are preferably present in molar ratios approximately as required to produce the desired zinc amino acid halide, although an excess of one material or another may be desirable in certain formulations, e.g., to balance pH against other formulation constituents, to provide additional antibacterial zinc, or to provide amino acid buffer. Preferably, however, the amount of halide is limited, as constraining the level of halide somewhat encourages interaction between the zinc and the amino acid.

In some embodiments, the total amount of zinc in the composition is 0.05 to 8% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition, e.g. about 0.84%.

In certain embodiments, a molar ratio of zinc to amino acid is at least 2:1. In other embodiments, the molar ratio is at least 1:1, at least 1:2, at least 1:3, at least 1:4, 2:1 to 1:4, 1:1 to 1:4, 1:2 to 1:4, 1:3 to 1:4, 2:1 to 1:3, 2:1 to 1:2, 2:1 to 1:1, or 1:3. Above 1:4, it is expected that the zinc will be totally dissolved.

The carrier represents all other materials in the composition other than the zinc amino acid halide complex or its precursors. The amount of carrier is then the amount to reach 100% by adding to the weight of the zinc amino acid halide, including any precursors.

Active Agents: The compositions disclosed herein may comprise various agents which are active to protect and enhance the strength and integrity of the enamel and tooth structure and/or to reduce bacteria and associated tooth decay and/or gum disease, including or in addition to the zinc-amino acid-halide complexes. Effective concentration of the active ingredients used herein will depend on the particular agent and the delivery system used. It is understood that a toothpaste for example will typically be diluted with water upon use, while a mouth rinse typically will not be. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., about 0.1 to about 20 wt % (expressed as weight of free base), e.g., about 1 to about 10 wt % for a consumer toothpaste or about 7 to about 20 wt % for a professional or prescription treatment product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly, with levels used in toothpaste being e.g., about 5 to about 15 times greater than used in mouthrinse. For example, a triclosan toothpaste may contain about 0.3 wt % triclosan.

Fluoride Ion Source: The oral care compositions may further include one or more fluoride ion sources, e.g., soluble fluoride salts. A wide variety of fluoride ion-yielding materials can be employed as sources of soluble fluoride in the present compositions. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments, the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment, or about 0.03 wt. % to about 5 wt. % in another embodiment, or about 0.1 wt. % to about 1 wt. % by weight of the composition in another embodiment. Weights of fluoride salts to provide the appropriate level of fluoride ion will obviously vary based on the weight of the counterion in the salt. In one embodiment, the composition contains sodium fluoride as a fluoride source in an amount of 0.03% to 5%, or 0.1% to 1% by weight of the composition, or about 0.32% by weight of the composition.

Abrasives: The compositions disclosed herein, may include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Other silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 114 and 165. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. In one embodiment, the compositions contain Foaming Agents: The oral care compositions disclosed herein also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

Surfactants: The compositions disclosed herein may contain anionic surfactants, for example:
i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
ii. higher alkyl sulfates, such as sodium lauryl sulfate,
iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$.
iv. higher alkyl aryl sulfonates such as sodium dodecyl benzene sulfonate (sodium lauryl benzene sulfonate)
v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Tartar Control Agents: In various embodiments, the compositions disclosed herein may comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The invention thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate $(Na_4P_2O_7)$, calcium pyrophosphate $(Ca_2P_2O_7)$, and sodium phosphate dibasic $(Na_2HPO_4)$, e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP)($NaSP_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents: The oral care compositions disclosed herein may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight e.g. about 0.5 to about 1.5% by weight.

Polymers: The oral care compositions disclosed herein may also include additional polymers to adjust the viscosity of the formulation or enhance the solubility of other ingredients. Such additional polymers include polysaccharides (e.g., cellulose derivatives, for example carboxymethyl cellulose, or polysaccharide gums, for example xanthan gum or carrageenan gum), and polyvinyl pyrrolidone. Acidic polymers, for example polyacrylate gels, may be provided in the form of their free acids or partially or fully neutralized water soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water-soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of 0.5% to 5.0% by weight of the total composition are used.

The compositions disclosed herein may include an anionic polymer, for example in an amount of from about 0.05 to about 5%. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000. Another useful class of polymeric agents includes polyamino acids containing proportions of anionic surface-active amino acids such as aspartic acid, glutamic acid and phosphoserine.

The term average molecular weight of a polymer is the total weight of its sample divided by the number of molecules in the sample, i.e., $\Sigma N_i M_i / \Sigma N_i$, and those skilled in the art can readily calculate the value using molecular weight values determined by size exclusion chromatograph or MALDI mass spectrometry.

Water: The oral compositions may comprise significant levels of water. Water employed in the preparation of commercial oral compositions should be deionized and free of organic impurities. The amount of water in the compositions includes the free water which is added plus that amount which is introduced with other materials.

Humectants: Within certain embodiments of the oral compositions, it is also desirable to incorporate a humectant to prevent the composition from hardening upon exposure to air. Certain humectants can also impart desirable sweetness or flavor to the compositions. Suitable humectants include edible polyhydric alcohols such as polyethylene glycol, e.g., PEG 600, glycerine, sorbitol, xylitol, propylene glycol as well as other polyols and mixtures of these humectants. In one embodiment of the disclosure, the oral compositions contain a structuring humectant, wherein the structuring humectant is PEG and PG, which are both present in an amount of 1-10% by weight of the composition. Preferably, PEG is present in an amount of 2-4% by weight of the composition and PG in an amount of 3-5% by weight of the composition. More preferably, PEG is present in an amount of about 3% by weight of the composition and PG in an amount of about 4% by weight of the composition.

Other Optional Ingredients:

In addition to the above-described components, the embodiments of the compositions disclosed herein can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents.

Unless stated otherwise, all percentages of composition components given in this specification are by weight based on a total composition or formulation weight of 100%.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

U.S. Patent Application Publication 2015/0328118 and PCT Publication WO 2014/098826, incorporated herein by reference, present experimental data demonstrating the ability of oral care compositions comprising ZLC to precipitate insoluble zinc compounds and to occlude dentinal tubules, thus making them useful in the treatment of dentinal hypersensitivity.

Several test toothpaste compositions comprising zinc-lysine complex (ZLC) are prepared and evaluated in room temperature aging studies and accelerated aging studies. After the designated period of time at the selected temperature, the viscosity of the compositions is measured by determining the yield stress of the compositions. The viscosity is measured by a Brookfield Viscometer using SpindleV74. Tables 1-4 show the compositions tested, and Tables 5-8 show test results.

Control toothpaste Formula 1 containing neither PEG 600 nor PG is shown in Table 1.

TABLE 1

| Ingredients | Formula 1 (wt %) |
|---|---|
| Demineralized Water | Balance |
| Sucralose | 0.02 |
| Sodium Saccharin | 0.20 |
| Sodium Fluoride | 0.32 |
| Sodium Tripolyphosphate | 2.00 |
| Glycerin | 47.56 |
| Polyethylene Glycol 600 | 0.00 |
| Propylene Glycol | 0.00 |
| Xanthan Gum | 0.1 |
| Polyvinyl Pyrrolidone | 1.0 |
| Silica Abrasive/cleaning | 22.0 |
| $TiO_2$ | 0.40 |
| ZLC complex | 5.77 |
| 35% Hydrochloric Acid | 0.68 |
| Sodium Hydroxide (50%) | 0.50 |
| Anionic Surfactant | 1.75 |
| Zwitterionic Surfactant | 1.00 |
| Flavor | 1.70 |
| Total Components | 100.00 |

Toothpaste Formulae 2-3 containing no PEG are shown in Table 2.

TABLE 2

| Ingredients | Formula 2 (wt %) | Formula 3 (wt %) |
|---|---|---|
| Demineralized Water | Balance | Balance |
| Sucralose | 0.02 | 0.02 |
| Sodium Saccharin | 0.20 | 0.20 |
| Sodium Fluoride | 0.32 | 0.32 |
| Sodium Tripolyphosphate | 2.00 | 2.00 |
| Glycerin | 43.56 | 40.56 |
| Polyethylene Glycol 600 | 0.00 | 0.00 |
| Propylene Glycol | 4.00 | 7.00 |
| Xanthan Gum | 0.1 | 0.1 |
| Polyvinyl Pyrrolidone | 1.0 | 1.0 |
| Silica Abrasive/cleaning | 22.0 | 22.0 |
| $TiO_2$ | 0.40 | 0.40 |
| ZLC complex | 5.77 | 5.77 |
| 35% Hydrochloric Acid | 0.68 | 0.68 |
| Sodium Hydroxide (50%) | 0.50 | 0.50 |
| Anionic Surfactant | 1.75 | 1.75 |
| Zwitterionic Surfactant | 1.00 | 1.00 |
| Flavor | 1.70 | 1.70 |
| Total Components | 100.00 | 100.00 |

Toothpaste Formulae 4-6 containing no PG are shown in Table 3.

TABLE 3

| Ingredients | Formula 4 (wt %) | Formula 5 (wt %) | Formula 6 (wt %) |
|---|---|---|---|
| Demineralized Water | Balance | Balance | Balance |
| Sucralose | 0.02 | 0.02 | 0.02 |
| Sodium Saccharin | 0.20 | 0.20 | 0.20 |
| Sodium Fluoride | 0.32 | 0.32 | 0.32 |
| Sodium Tripolyphosphate | 2.00 | 2.00 | 2.00 |
| Glycerin | 48.31 | 46.81 | 44.31 |
| Polyethylene Glycol 600 | 3.00 | 4.50 | 7.00 |
| Propylene Glycol | 0.00 | 0.00 | 0.00 |
| Xanthan Gum | 0.1 | 0.1 | 0.1 |
| Carboxymethylcelullose Sodium | 0.3 | 0.3 | 0.3 |
| Polyvinyl Pyrrolidone | 1.25 | 1.25 | 1.25 |
| Silica Abrasive/cleaning | 18.0 | 18.0 | 18.0 |
| $TiO_2$ | 0.40 | 0.40 | 0.40 |
| 85% Syrup phosphoric acid | 0.20 | 0.20 | 0.20 |
| ZLC complex | 5.77 | 5.77 | 5.77 |
| 35% Hydrochloric Acid | 0.68 | 0.68 | 0.68 |
| Anionic Surfactant | 1.75 | 1.75 | 1.75 |
| Zwitterionic Surfactant | 1.00 | 1.00 | 1.00 |
| Flavor | 1.70 | 1.70 | 1.70 |
| Total Components | 100.00 | 100.00 | 100.00 |

Toothpaste Formula 7 containing 3% PEG 600 and 4% PG is shown in Table 4.

TABLE 4

| Ingredients | Formula 7 (wt %) |
|---|---|
| Demineralized Water | Balance |
| Sucralose | 0.02 |
| Sodium Saccharin | 0.20 |
| Sodium Fluoride | 0.32 |
| Sodium Tripolyphosphate | 2.00 |
| Glycerin | 40.56 |
| Polyethylene Glycol 600 | 3.00 |
| Propylene Glycol | 4.00 |
| Xanthan Gum | 0.1 |
| Polyvinyl Pyrrolidone | 1.0 |
| Silica Abrasive/cleaning | 22.0 |
| $TiO_2$ | 0.40 |
| ZLC complex | 5.77 |
| 35% Hydrochloric Acid | 0.68 |
| Sodium Hydroxide (50%) | 0.50 |
| Anionic Surfactant | 1.75 |
| Zwitterionic Surfactant | 1.00 |
| Flavor | 1.70 |
| Total Components | 100.00 |

Yield stress test results of Formula 1 are shown in Table 5.

TABLE 5

| | Formula 1 | |
|---|---|---|
| Duration | Temperature | Yield Stress cPs at 1 RPM |
| Initial | | 235755 |
| 1 month | CRT | 70851 |
| | 40° C. | 47664 |
| | 49° C. | 59258 |

Formula 1, which contains neither PEG 600 nor PG, is shown to become less viscous at room temperature, 40° C., and 49° C. aging for 1 month, and complete loss of yield stress and stand up within 1 week.

Yield stress test results of Formulae 2 and 3 are shown in Table 6

TABLE 6

| | | Yield Stress cPs at 1 RPM | |
|---|---|---|---|
| Duration | Temperature | Formula 2 | Formula 3 |
| Initial | | 600953 | 533966 |
| 1 month | CRT | 36070 | 302731 |
| | 40° C. | 36070 | 111431 |
| | 49° C. | 47664 | 105634 |

Like control Formula 1, Formulae 2 and 3, which contain no PEG but contain 4% PG and 7% PG respectively, are shown to become less viscous at room temperature, 40° C., and 49° C. aging for 1 month, and complete loss of yield stress and stand up within 1 week.

Yield stress test results of Formulae 4-6 are shown in Table 7.

TABLE 7

| | | Yield Stress cPs at 1 RPM | |
|---|---|---|---|
| Duration | Temperature | Formula 5 | Formula 6 |
| Initial | | 512598 | 61740 |
| 1 week | CRT | 366753 | 111584 |
| 1 month | CRT | | 129428 |
| | 40° C. | | 81844 |
| | 49° C. | | 81844 |
| 3 months | CRT | | 363239 |
| | 40° C. | | 56578 |
| | 49° C. | | 50781 |

Formula 4 that contains no PG but 3% PEG shows immediate separation turning in to thin consistency, while Formula 5 that contains no PG but 4.5% PEG shows phase separation at room temperature aging for 1 week. However, Formula 6. which contains no PG but 7% PEG, built some viscosity at room temperature aging for 1 week, 1 month and 3 months, and appearance of gel ball texture at 40° C. 3 months, demonstrating that higher PEG 600 increases incidence of texture/gelation look.

The above yield stress test results of Formulae 2-6 show that the removal of either PEG or PG cause complete loss of yield stress (stand up) and viscosity within 1 week at room temperature.

Yield stress test results of Formula 7 are shown in Table 8.

TABLE 8

| Duration | Temperature | Yield Stress cPs at 1 RPM |
|---|---|---|
| Initial | | 269095 |
| 1 month | CRT | 531390 |
| | 40° C. | 589359 |
| | 49° C. | 552001 |
| 2 months | CRT | 485177 |
| | 40° C. | 583562 |
| | 49° C. | 497896 |

In contrast with the other formulae, Formula 7, which contains 3% PEG and contains 4% PG, is surprisingly shown to become more viscous across all the tested temperatures—at room temperature, 40° C., 49° C. aging for 1 month and 2 months, improved viscosity and a complete retention of the viscosity and yield stress (stand-up).

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

What is claimed is:

1. A toothpaste composition comprising
   a. zinc in complex with an amino acid, and
   b. a humectant system comprising a structuring humectant, wherein the structuring humectant is polyethylene glycol (PEG) in an amount of 1-10% by weight of the toothpaste composition and propylene glycol (PG) in an amount of 1-10% by weight of the toothpaste composition; and
   c. an organic or inorganic acid selected from one or more of phosphoric acid, hydrochloric acid and citric acid; wherein the composition has a stable yield stress for one month as measured by a Brookfield Viscometer using Spindle V74 at 1 RPM.

2. The toothpaste composition of claim 1, wherein the amino acid is selected from lysine, arginine, and glycine in free or salt form.

3. The toothpaste composition of claim 2, wherein the amino acid is lysine in free or salt form.

4. The toothpaste composition of claim 1, wherein the zinc amino acid complex is a zinc lysine chloride complex or a zinc arginine chloride complex.

5. The toothpaste composition of claim 1, wherein the zinc amino acid complex is a zinc lysine chloride complex having the chemical structure $[Zn(C_6H_{14}N_2O_2)_2Cl]^+Cl^-$ ("ZLC"), either in solution of the cationic complex ($[Zn(C_6H_{14}N_2O_2)_2Cl]^+$) and the chloride anion, or in solid salt form, optionally in mono- or dihydrate form.

6. The toothpaste composition of claim 1, wherein the zinc amino acid complex is present in an amount of 2-10% by weight of the tooth paste composition.

7. The toothpaste composition of claim 1, wherein the PEG is present in an amount of 2-4% by weight of the toothpaste composition and the PG is present in an amount of 3-5% by weight of the toothpaste composition.

8. The toothpaste composition of claim 1, wherein the PEG is present in an amount of about 3% by weight of the toothpaste composition and the PG in an amount of about 4% by weight of the toothpaste composition.

9. The toothpaste composition of claim 1, wherein the PEG is PEG 600.

10. The toothpaste composition of claim 1, wherein the composition comprises the acid in an amount of from 0.05 to 5% by weight of the composition.

11. The toothpaste composition of claim 1, further comprising sodium tripolyphosphate.

12. The toothpaste composition of claim 1, comprising ingredients selected from one or more of abrasives, buffering agents, surfactants, thickeners, gum strips or fragments, breath fresheners, flavoring, fragrance, coloring, antibacterial agents, whitening agents, agents that interfere with or prevents bacterial attachment, calcium sources, orally acceptable potassium salts, and anionic polymers.

13. The toothpaste composition of claim 1 comprising an effective amount of a fluoride ion source.

14. A method of improving the rheological stability of a toothpaste composition comprising formulating the toothpaste composition with zinc in complex with an amino acid, and 1-10% by weight of propylene glycol (PG) and 1-10% by weight of polyethylene glycol (PEG), and adding an acid selected from one or more of phosphoric acid, hydrochloric acid and citric acid, wherein the method results in a composition according to claim 1.

15. The method of claim 14, wherein the zinc amino acid complex is a zinc lysine chloride complex or a zinc arginine chloride complex.

16. The method of claim 14, wherein the zinc amino acid complex is present in an amount of 2-10% by weight of the tooth paste composition.

17. The method of claim 14, wherein the PEG is present in an amount of about 3% by weight of the toothpaste composition and the PG in an amount of about 4% by weight of the toothpaste composition.

18. The method of claim 14, wherein the acid is added in an amount of from 0.05 to 5% by weight of the composition.

19. The composition of claim 1, wherein the acid is hydrochloric acid.

20. The composition of claim 1, wherein the acid is hydrochloric acid present in an amount of from 0.05 to 5% by weight of the composition.

* * * * *

UNITED STATES PATENT AND TRADEMARK OFFICE
CERTIFICATE OF CORRECTION

PATENT NO. : 10,485,742 B2
APPLICATION NO. : 15/828787
DATED : November 26, 2019
INVENTOR(S) : Neeta Atul Patel et al.

Page 1 of 1

It is certified that error appears in the above-identified patent and that said Letters Patent is hereby corrected as shown below:

In the Specification

In Column 8, Line 4, "1%-100%" should be changed to --1%-10%--

Signed and Sealed this
Seventeenth Day of March, 2020

Andrei Iancu
*Director of the United States Patent and Trademark Office*